US012788249B2

(12) United States Patent
Loock et al.

(10) Patent No.: US 12,788,249 B2
(45) Date of Patent: Nov. 10, 2026

(54) HADAMARD-TRANSFORM FLUORESCENCE EXCITATION-EMISSION-MATRIX IMAGING SYSTEMS

(71) Applicants: Hans-Peter Loock, Victoria (CA); Oren Katz, Victoria (CA)

(72) Inventors: Hans-Peter Loock, Victoria (CA); Oren Katz, Victoria (CA)

(73) Assignee: UVic Industry Partnerships Inc., Victoria (CA)

( * ) Notice: Subject to any disclaimer, the term of this patent is extended or adjusted under 35 U.S.C. 154(b) by 511 days.

(21) Appl. No.: 18/194,373

(22) Filed: Mar. 31, 2023

(65) Prior Publication Data

US 2023/0309834 A1 Oct. 5, 2023

Related U.S. Application Data

(60) Provisional application No. 63/362,330, filed on Mar. 31, 2022.

(51) Int. Cl.
*G01J 3/44* (2006.01)
*A61B 1/04* (2006.01)
*A61B 5/00* (2006.01)

(52) U.S. Cl.
CPC ............ *A61B 5/0059* (2013.01); *A61B 1/043* (2013.01)

(58) Field of Classification Search
CPC .......... G01J 3/44; G01J 3/4406; G01J 3/2003; G01J 3/2826; F01J 3/4406; G01N 21/65;
(Continued)

(56) References Cited

U.S. PATENT DOCUMENTS

2006/0050278 A1* 3/2006 Treado ................. G01N 21/255 356/417
2010/0154620 A1 6/2010 Loock et al.
2017/0052118 A1* 2/2017 Loock ..................... G01J 3/021

FOREIGN PATENT DOCUMENTS

EP 2453253 A1 * 5/2012 ............. G01S 17/42
WO WO-2020028367 A1 * 2/2020 ........... A61B 1/0684

OTHER PUBLICATIONS

Sigernes et al., "Do it yourself hyperspectral imager for handheld to airborne operations," Optics Express, 26(5) pp. 6021-6035 (Mar. 2018).

(Continued)

*Primary Examiner* — Abdullahi Nur
(74) *Attorney, Agent, or Firm* — Klarquist Sparkman, LLP

(57) ABSTRACT

Multi-spectral imaging systems include an excitation light source that produces an excitation beam having an excitation light spectrum. A programmable light source sequentially selects three or more excitation wavelength ranges from a plurality of excitation wavelength ranges based on code words defined by a selected code. Based on the code words, a sequence of encoded excitation beams is produced which are sequentially directed to a sample location. An imaging system such as a hyperspectral camera is situated to produce spectral images of a sample associated with a plurality of emission wavelength ranges in response to each of the encoded excitation beams. The spectral images are decoded to produce a spectral emission image corresponding to emitted intensity at the plurality of emission wavelengths as a function of excitation wavelength.

25 Claims, 8 Drawing Sheets

(58) Field of Classification Search
CPC . G01N 21/645; G01N 21/255; G01N 21/6458
See application file for complete search history.

(56) References Cited

OTHER PUBLICATIONS

Ferguson et al. "HPLC-detector based on Hadamard-transform fluorescence excitation-emission-matrix spectroscopy," Analytical Chemistry 93(23) pp. 8116-8121 (Jun. 2021).

* cited by examiner

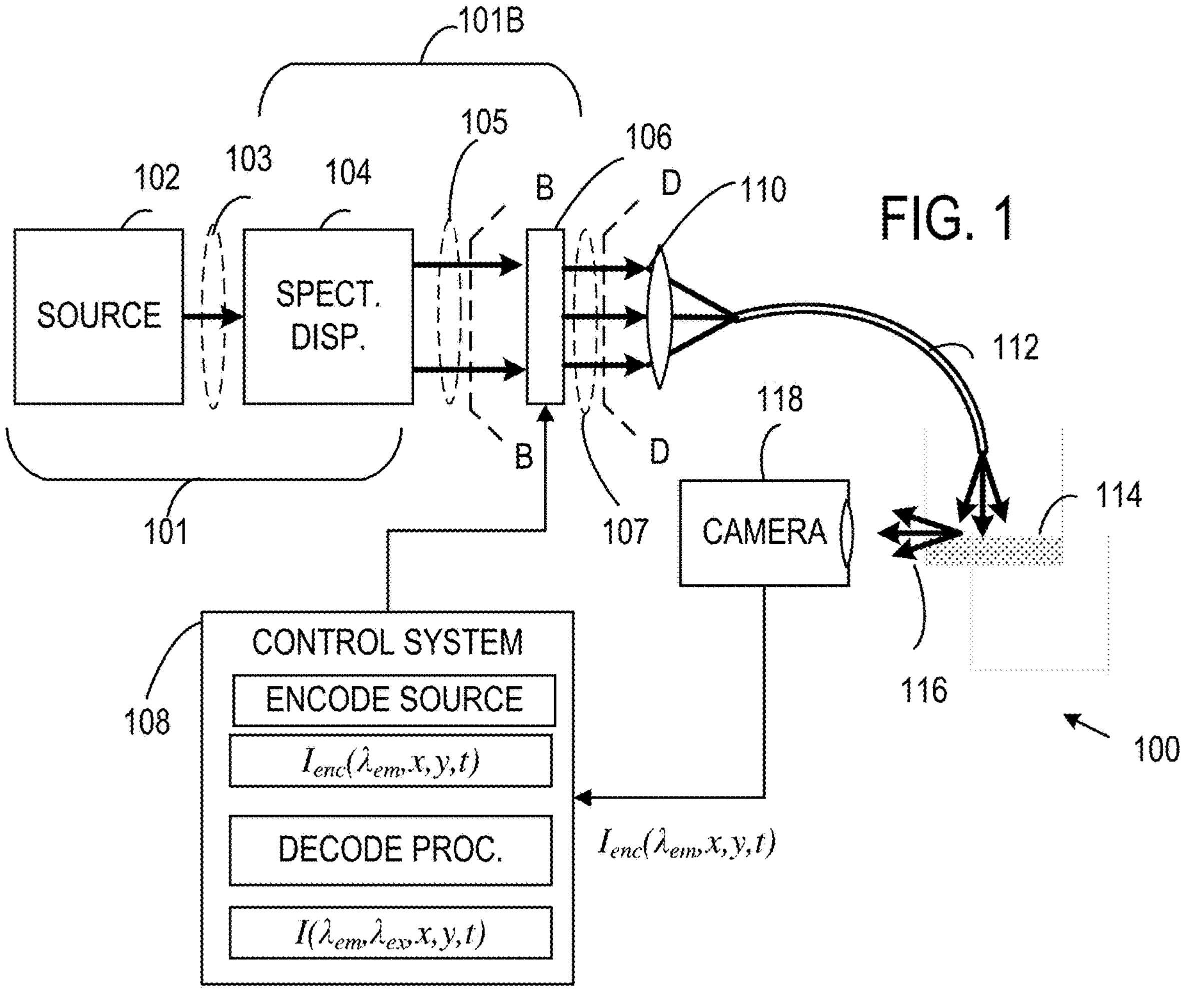
FIG. 1
FIG. 1B
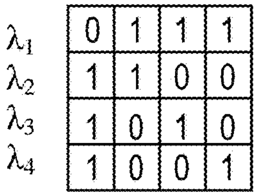
FIG. 1C
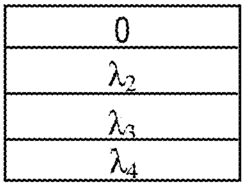
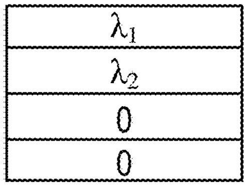
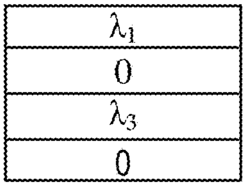
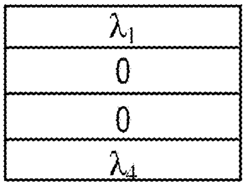
FIG. 1D1 FIG. 1D2 FIG. 1D3 FIG. 1D4

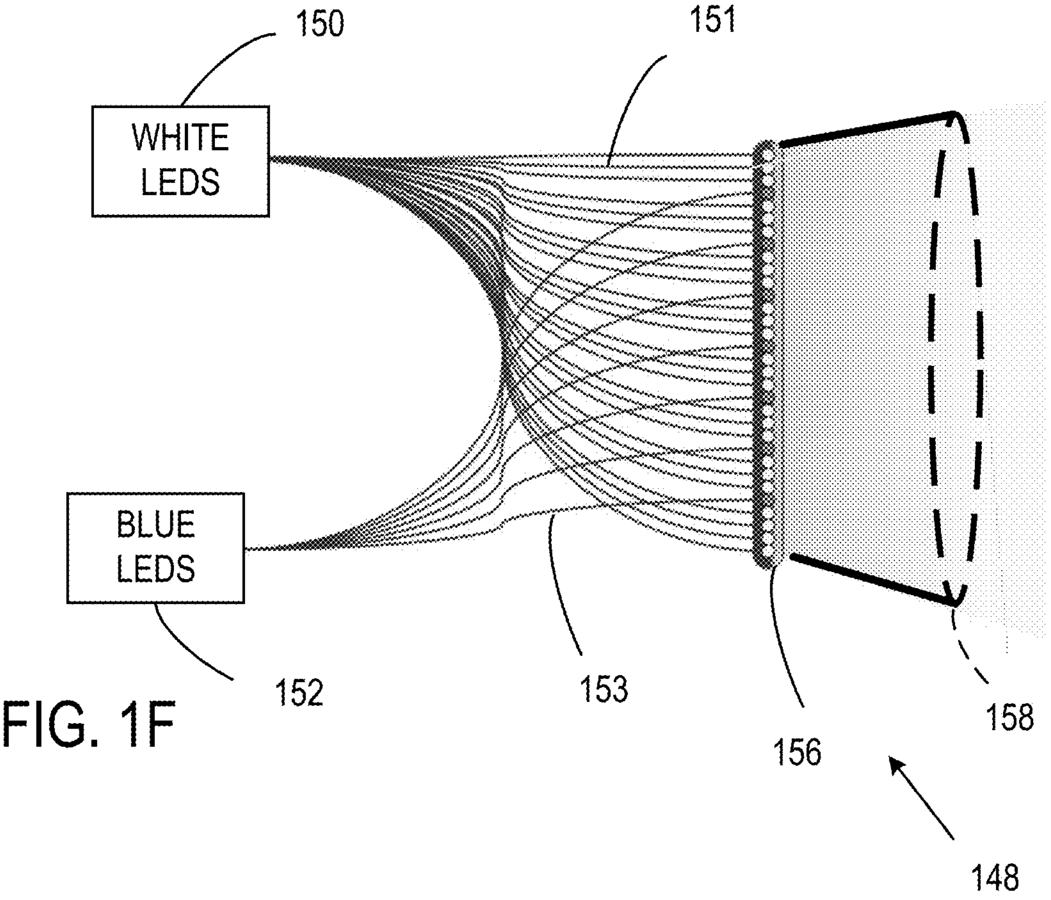
FIG. 1F
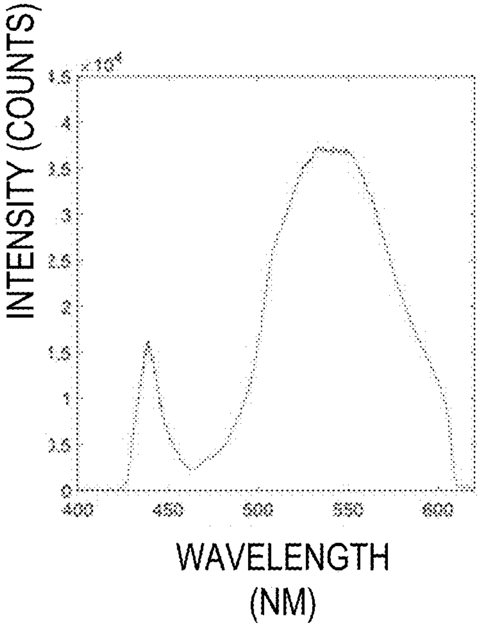
FIG. 1E1
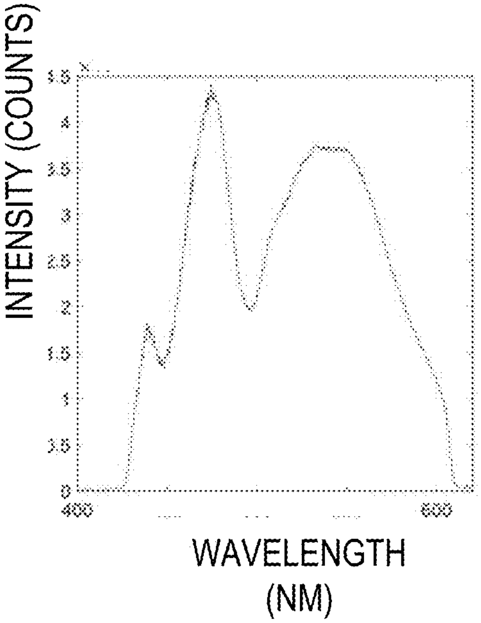
FIG. 1E2

302

PROGRAMMABLE LIGHT SOURCE
308.
304
SAMPLE
HYPERSPECTRAL CAMERA
306
310
312
MEMORY
$I_1(\lambda_{em},x,y,t)$
.
.
$I_N(\lambda_{em},x,y,t)$
PROCESSOR
$I(\lambda_{em},x,y,t)$
SPECTRAL COMPONENT SELECTIONS
1, 2, . . . N
320
SAMPLE CHARACTERIZATION SYSTEM
303
300

HADAMARD-TRANSFORM FLUORESCENCE EXCITATION-EMISSION-MATRIX IMAGING SYSTEMS

CROSS-REFERENCE TO RELATED APPLICATIONS

This application claims the benefit of U.S. Provisional Patent Application 63/362,330, filed Mar. 31, 2022, which is incorporated herein by reference.

FIELD

The disclosure pertains to excitation-emission matrix spectroscopy.

BACKGROUND

Fluorescence spectroscopy is commonly used to detect and identify molecules in a mixture by exciting a chemical or biological sample with a laser and measuring the emission spectra produced in response. More accurate identification is possible if many excitation wavelengths are used, and the emission spectra given by the light intensity at range of emission wavelengths $\lambda_{em}$ are detected at multiple excitation wavelengths $\lambda_{ex}$. The resulting two-dimensional spectra (i.e., the intensities, I, for each ($\lambda_{ex}$,$\lambda_{em}$) pair) are called an excitation emission matrix (EEM) and provide a characteristic fingerprint for many molecules. However, EEM spectroscopy is very slow, because a scan is performed by stepping through the wavelengths sequentially. EEM acquisitions often have low signal-to-noise ratios, further limiting their usefulness. Conventional EEM approaches cannot be coupled to imaging systems needed to characterize spatially extended or spatially heterogeneous samples. In view of these shortcomings, alternative approaches are needed.

BRIEF DESCRIPTION OF THE DRAWINGS

FIG. 1 illustrates a representative multi-spectral imaging system.

FIG. 1B illustrates representative wavelength ranges used in the apparatus of FIG. 1.

FIG. 1C illustrates a representative code.

FIGS. 1D1-1D4 illustrate excitation encodings based on the code of FIG. 1C.

FIG. 1E1 is a spectrum of a representative LED output having a white appearance.

FIG. 1E2 is a spectrum of a combination of a white light LED and a blue light LED.

FIG. 1F illustrates an arrangement of LEDs arranged to be situated at a slit of a multiplexer for use as programmable light source.

FIG. 2 illustrates a representative multi-spectral imaging method.

FIG. 4 illustrates a portion of a representative sensor for hyperspectral imager.

DETAILED DESCRIPTION

Figure 2:
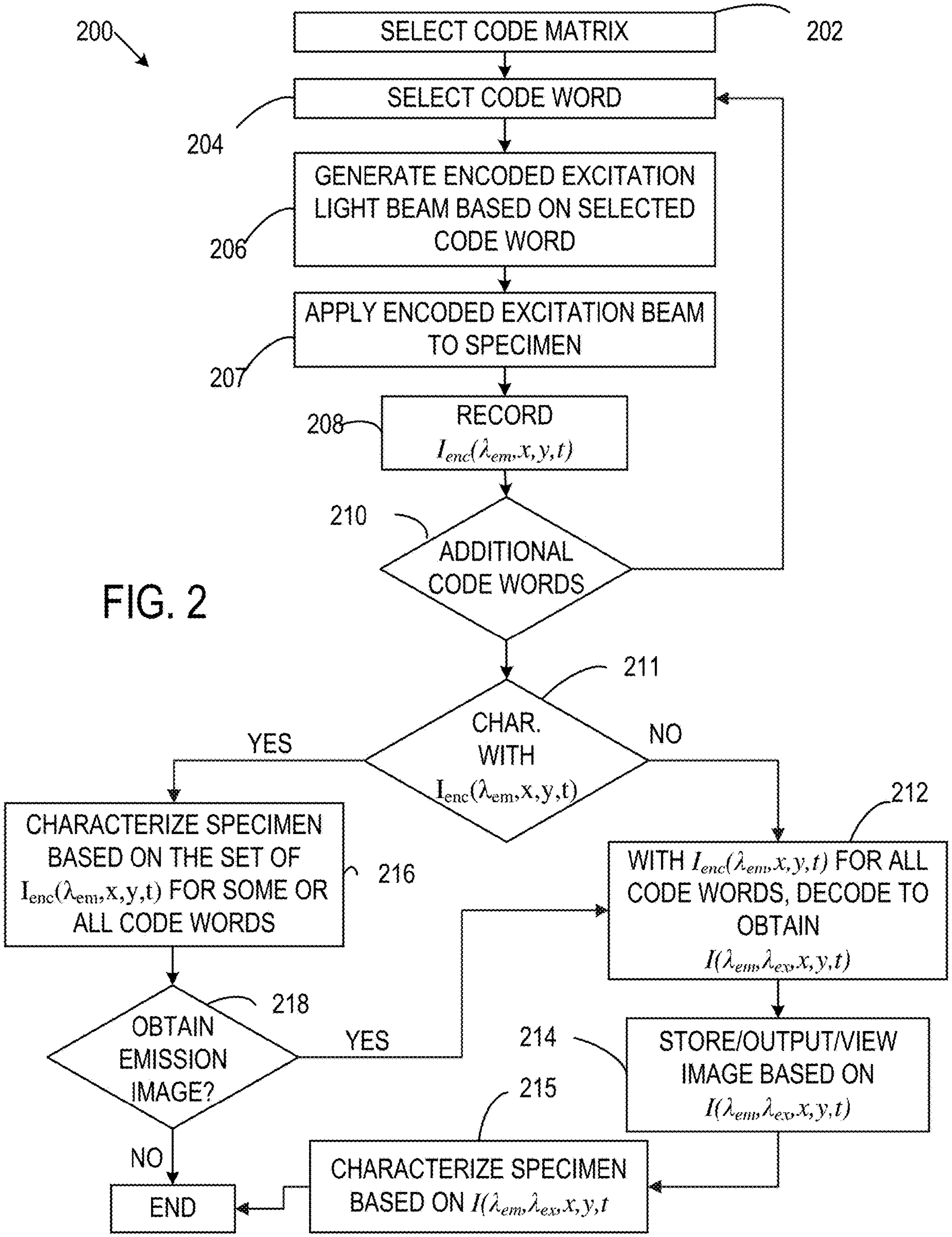

Multiplexing techniques using the Hadamard transform (HT) to sample multiple excitation wavelengths at a time have been developed. Using a fully programmable light source, a user can select any combination of excitation wavelengths, reducing acquisition time for an EEM. Such systems are described in Loock et al., U.S. Pat. No. 10,481,092 and Ferguson et al., "HPLC-Detector Based on Hadamard-Transform Fluorescence Excitation-Emission-Matrix Spectroscopy," both of which are incorporated herein by reference.

Disclosed herein are hyperspectral imaging systems which allow the collection of an EEM spectrum with every (x, y) pixel of an image such as a digital camera image, or selected pixels of such images. With these systems, the identification and characterization of chemical compounds through their EEM spectra and other application of EEM can be based on an image of a spatially distributed sample obtained using a programmable light source. The spatially distributed sample can be a petri dish or an agar plate, a 96-well reaction plate, a biological system (leaf, tissue), or the result of a chemical separation process (thin film chromatogram, gel electropherogram), to mention a few examples. Small samples can be examined by optical microscopy.

The methods and apparatus disclosed herein can be based on HT EEM spectroscopy to allow four-dimensional images to be captured in seconds. Thus, sequential images are acquired through a fifth dimension of time (x, y, $\lambda_{ex}$, $\lambda_{em}$, t) and time-dependent processes may be monitored and spatially resolved. This allows for applications in process control, microfluidics, chemical and biological kinetics, etc. Applications include fluorescence microscopy, where cells, tissue, or microfluidic devices can be imaged using the hyperspectral camera connected to a microscope lens. Whereas a conventional microscope would only provide information spatially (and limited spectral data), the disclosed approaches allow for separating out components not only in space but also into their component EEM spectra. In some examples, the disclosed approaches can be applied to imaging of kinetics multiplexed by high throughput assays. Since each pixel is one full EEM, the kinetics of separate samples can be run in parallel if they fit within the field of view of the camera. For example, the kinetics of 96 individual reactions could be monitored if a single 96 well-plate were placed in view of the camera and illuminated by the light source. Generally, using Hadamard matrix based or other encodings and inverse Hadamard transforms or other inverse operations, chemical or other information based on multivariate analysis of a four-dimensional data "cube" I(x, y, $\lambda_{ex}$, $\lambda_{em}$) can be obtained, wherein I is measured intensity, x and y are spatial coordinates, and $\lambda_{ex}$ and $\lambda_{em}$ are emission and excitation wavelengths.

Selections of spectral components are generally based on a code set comprising a plurality of codes referred to herein as code words. The code words are generally linearly independent and, in many examples, orthogonal, to permit calculation of the emitted spectral intensity as a function of excitation wavelength. Codes can be binary codes based on, for example, Hadamard matrices, Walsh functions, binary simplex codes, or Golay codes.

Example 1. Hyperspectral Imaging

FIG. 1 illustrates a representative system 100 that includes an excitation light source 101, shown in this example as including a broadband light source 102 that produces a broadband or multiwavelength beam 103, and a spectral disperser 104 such as one or more diffraction gratings or one or more prisms or other spectral dispersers. The broadband light source 102 can include one or more emitters such as lamps, LEDS, and plasma light sources. In some examples, a series of emitters emitting different wavelengths of light can be used such as laser diodes or other lasers, LEDs, or combinations of lasers and LEDs. For use with grating-based spectral dispersion, emitters can be arranged in a linear array or otherwise to correspond to an entrance slit. In the example of FIG. 1, a spectrally dispersed beam 105 is coupled to a spatial light modulator (SLM) 106 such as, for example, a digital micro-mirror device (DMD) or a liquid crystal SLM. FIG. 1B illustrates a representative spectral dispersion produced by the spectral disperser 104 that shows four spectral components that extend along a common axis. The SLM 106 is operable to modulate the spectrally dispersed beam 105 to produce a wavelength-encoded beam 107 based on a suitable encoding provided by a control system 108 that typically includes a microprocessor or other logic device such an FPGA or PLD. A representative code is illustrated in FIG. 1C which is applied sequentially column by column to produce output encoded beams with encodings shown in FIGS. 1D1-1D4. This encoding is an example provided for explanation using only four wavelengths and a code of length 4 and other codes, typically longer codes, for encoding with many more wavelengths are used. Typical codes are based on Hadamard codes, or Walsh functions, having elements +1, −1 that are reduced to form S-codes having elements 0, +1. Because optical images are usually acquired based on signal intensities (and not signal amplitudes), 0, 1 codes are preferred. However, −1, +1 codes can be used based on subtraction of 0, 1 codes. A −1, +1 code can be used to produce a first 0, +1 subcode by assigning all −1 values to be 0 and a second +1,0 subcode by assigning all +1 values to be 0 and all −1 values to +1. Encoded intensities are obtained for each subcode and then these intensities are subtracted to produce an encoded intensity corresponding to a −1, +1 code. Because using such codes is less common in practice, −1, +1 codes are not discussed further.

For convenience, individual codes of a set of codes (such as shown in the columns of FIG. 1C) are referred to as code words. Using code words, the spectral disperser 104 and the SLM 106 form a multiplexer 101B that provides light in a combination of selected wavelength ranges. If multiple emitters are used with different wavelengths, the emitter can be modulated based on the selected code to provide multiplexing.

The encoded beam 107 can be focused by a lens 110 or other focusing optics into a beam delivery system 112 such as a light guide for delivery to a region of interest of a sample 114. In response to the encoded excitation beam, emitted light 116 is produced and received by a camera 118. The camera includes a pixel array and each pixel receives a portion of the emitted light 116 corresponding to a location in the sample. This emitted portion at each pixel is responsive to the encoded excitation beam and thus can include portions associated with sample response to each of the excitation beam wavelengths associated with the encoding. The camera 118 typically stores image data in an on-board non-transitory memory device and the image data is then communicated to a non-transitory computer-readable memory such as a hard disk or RAM drive associated with the control system 108. In this example with the code of FIG. 1C providing for the encoding of the excitation light, each pixel is associated with image intensities $I_{em}$ associated with emission at each of multiple wavelengths, and these intensities can be decoded to produce estimates of emission intensity responsive to each of the excitation wavelengths $\lambda_1$-$\lambda_4$. This can be done as a function of time to produce $I_{em}(\lambda_{ex}, x, y, t)$, wherein $I_{em}$ represents emitted intensity, and $\lambda_{ex}$, is excitation wavelength. Decoding of a set of encoded intensities $I_{encoded}$ represented as a linear array and obtain with a code matric C can be accomplished by the control system 108 as a matrix multiplication of an inverse of C with $I_{encoded}$, i.e., a set decoded intensities $I_{decoded}$ arranged in a linear array can be obtained as $I_{decoded}=(C^{-1})(I_{encoded})$.

While determination of $I_{em}(\lambda_{ex}, x, y, t)$ is useful, in many applications, intensity as a function of emission wavelength is also desirable, i.e., $I(\lambda_{ex}, \lambda_{em}, x, y, t)$. The separation of the emission light into many distinct wavelength ranges can be performed with a spectrally sensitive camera which can produce intensity values at three or more wavelengths. So-called hyperspectral cameras can be used such as disclosed in Hagen et al., Opt. Eng., vol. 52, 090901 (2013) and Sigernes et al, "Do it yourself hyperspectral imager for handheld to airborne operations," Opt. Express 5:6021-6035 (2018), both of which are incorporated herein by reference. Any camera having more than three distinct wavelength ranges is referred to herein as a "hyperspectral camera." In another example, a spectral resolving detector array (SRDA) can be used, typically including a CMOS or other image sensor and an associated filter array such as a Bayer filter. In SRDAs, a pixel comprises multiple photosensitive elements and corresponding filter segments, so that an SRDA can provide an output $I(\lambda_{em}\ y, t)$; dependence on $\lambda_{ex}$, can be produced by pixel level decoding to obtain $I(\lambda_{ex}, \lambda_{em}, x, y, t)$.

Example 2. Representative Broadband Light Source Using LEDs

FIGS. 1E1, 1E2, and IF illustrates an LED-based light source for use in the system 100. While so-called white light LEDs are available, their spectral emission typically has regions at or near 470 nm that exhibit reduced emitted power as shown in FIG. 1E1. However, such white emitting LEDs can be combined with LEDs that emit at or near these reduced power regions to fill in these spectral regions. For convenience, these LEDs are referred to as "blue" LEDs. FIG. 1E2 illustrates a spectrum associated with combining output of a white light LED and a blue LED showing elimination of the power dip near 470 nm. As shown in FIG. 1F, a light source 148 includes a plurality 150 of white LEDS and a plurality 152 of blue LEDs that are coupled to corresponding pluralities of optical fibers such as optical fibers 151, 153 having ends coupled to form a linear array 156. In the example of FIG. 1F, emission from a single blue LED is combined with the emission from a single white LED. In the linear array 156, seven fiber optic cable transmitting light from the blue LED are shown with dark shading and are interleaved with 25 fiber optical cables transmitting light from the white LED. The white and blue LEDs produce a beam 158 that can be directed to a multiplexer by, for example, situating the linear array 156 at an input slit or other input aperture for dispersion by a diffraction grating or prism, or using an optical system to image the linear array 156 at the slit.

Example 3. Code-Based EEM Imaging

Referring to FIG. 2, a representative method 200 includes selecting a code (typically represented as a Hadamard matrix or other matrix) at 202 and selecting code words from the code at 204, typically as rows or columns of a matrix representation of the code. At 206, the code word is used to produce an encoded excitation beam, wherein the code word specifies the wavelength ranges to be used. At 207, the encoded excitation beam is applied to a specimen and at 208, an excitation encoded image $I_{enc}(\lambda_{em}, x, y, t)$ is recorded using a camera or other apparatus that can spectrally resolve specimen emission. At 210 it is determined if images for additional code words are to be acquired as needed for decoding. If so, the method returns to 204 and a different code word is selected. If excitation encoded images for all code words have been obtained, at 211 it is determined if specimen characterization is to be based on the excitation encoded images without decoding. If so, the specimen is characterized at 216 based on some or all of the excitation encoded images. The excitation encoded images include all the information gathered in measurements and decoding need not be done in all cases. A database of excitation encoded image data can be used to compare measured values with stored values to find a suitable match. Alternatively, the excitation-encoded images can be directly subjected to mathematical analysis to identify the constituents of the sample, for example by using multivariate analysis of the $I_{enc}(\lambda_{em}, x, y, t)$ data cube. If the excitation encoded images are to be decoded as determined at 211, the excitation encoded images are decoded at 212 to produce excitation-emission matrix images at 212 which can be stored, transmitted, or viewed at 214 and used for specimen characterization at 215. In some examples, time dependence of excitation-emission images is desired, and the code is applied periodically, repetitively, or otherwise to produce time dependent excitation encoded and excitation-emission images.

Example 4. Code-Based Imaging

Figure 3:
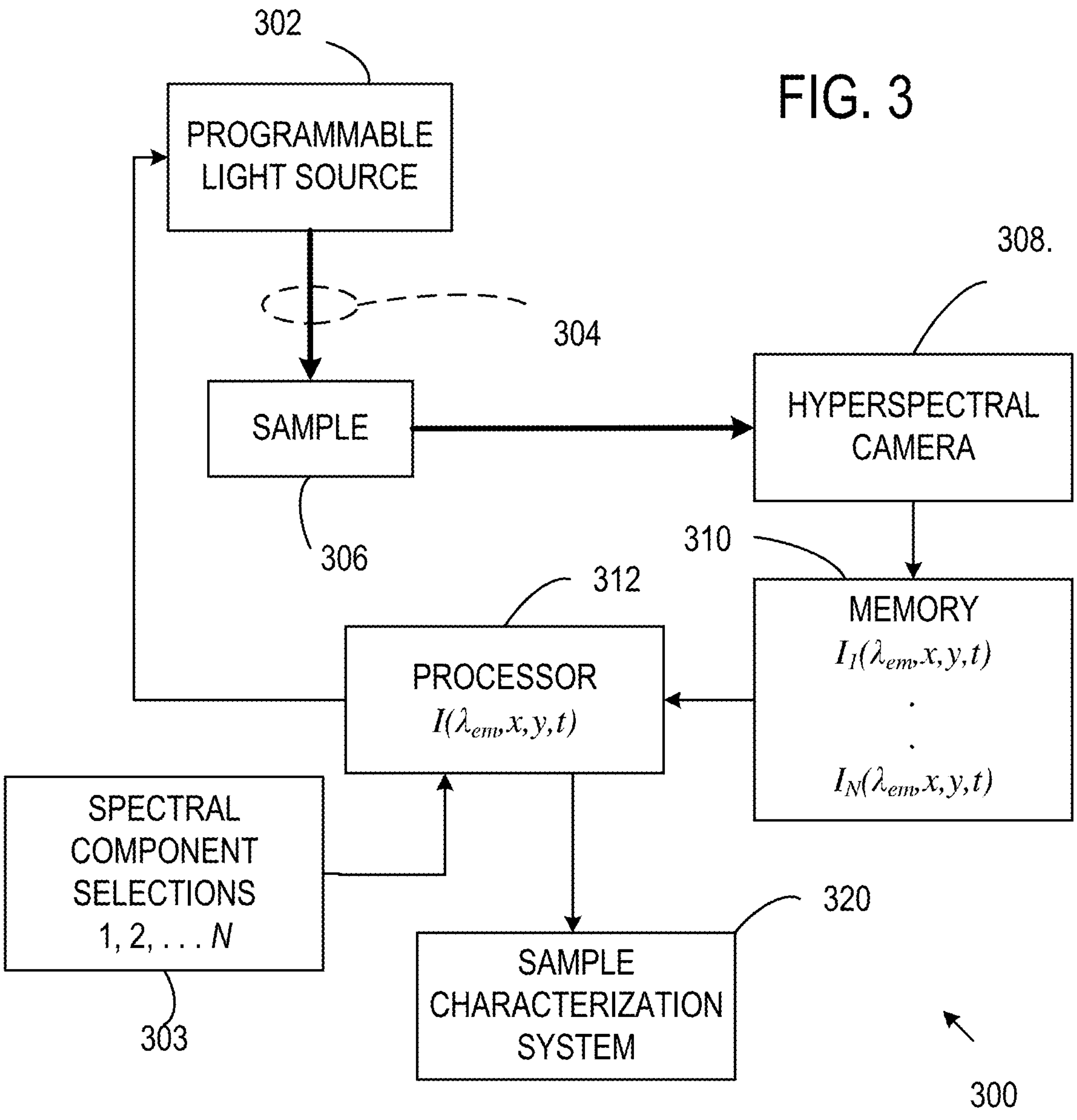
FIG. 3 illustrates a representative system for obtaining excitation-emission matrix spectra.

Referring to FIG. 3, a representative system 300 includes a programmable light source (PLS) 302 such as a broadband light source, a white light source or other light source which provides light that can be spectrally dispersed according to a first set of spectral components and selectively modulated to provide an optical beam 304 or an array of spectral emitters such as LEDs suitably modulated. The optical beam 304 then includes three or more selected spectral components (typically determined by a code word) and is directed to a sample 306 and a hyperspectral camera 308 that produces a spectral image $I_1(\lambda_{em}, x, y, t)$ responsive to the first selected set of spectral components of the optical beam 304, wherein x, y refer to sample locations as imaged to pixel locations in the hyperspectral camera 308, $\lambda_{em}$, is emission wavelength and $I_1$ is intensity measured in response to the first set of selected spectral components of the optical beam 304. A memory 310 such as RAM or other non-transitory memory is coupled to store the spectral image $I_1(\lambda_{em}, x, y, t)$.

Additional sets (2, . . . , N) of spectral components are then provided by the PLS 302 in the same manner to obtain corresponding spectral images $I_2(\lambda_{em}, x, y, t), \ldots, I_N(\lambda_{em}, x, y, t)$ which are similarly stored in the memory 310 as $I_{encoded}=I(\lambda_{em}, N, x, y, t)$. The stored spectral images are coupled to the processor 312 that is operable to determine emitted spectral intensity as a function of excitation wavelength, i.e., to determine $I_{decoded}=I(\lambda_{em}, \lambda_{ex}, x, y)$, wherein $\lambda_{ex}$ is excitation wavelength. In typical examples, selections of spectral components or codes used to select spectral components are stored in non-transitory memory 303 and coupled by the processor 312 to the PLS 302. The emitted spectral intensity as a function of excitation wavelength can be directed to a sample characterization system 320 to extract sample properties. In some cases, the processor 312 is programmed to do this.

Example 5. Representative Hyperspectral Camera

Figure 4:
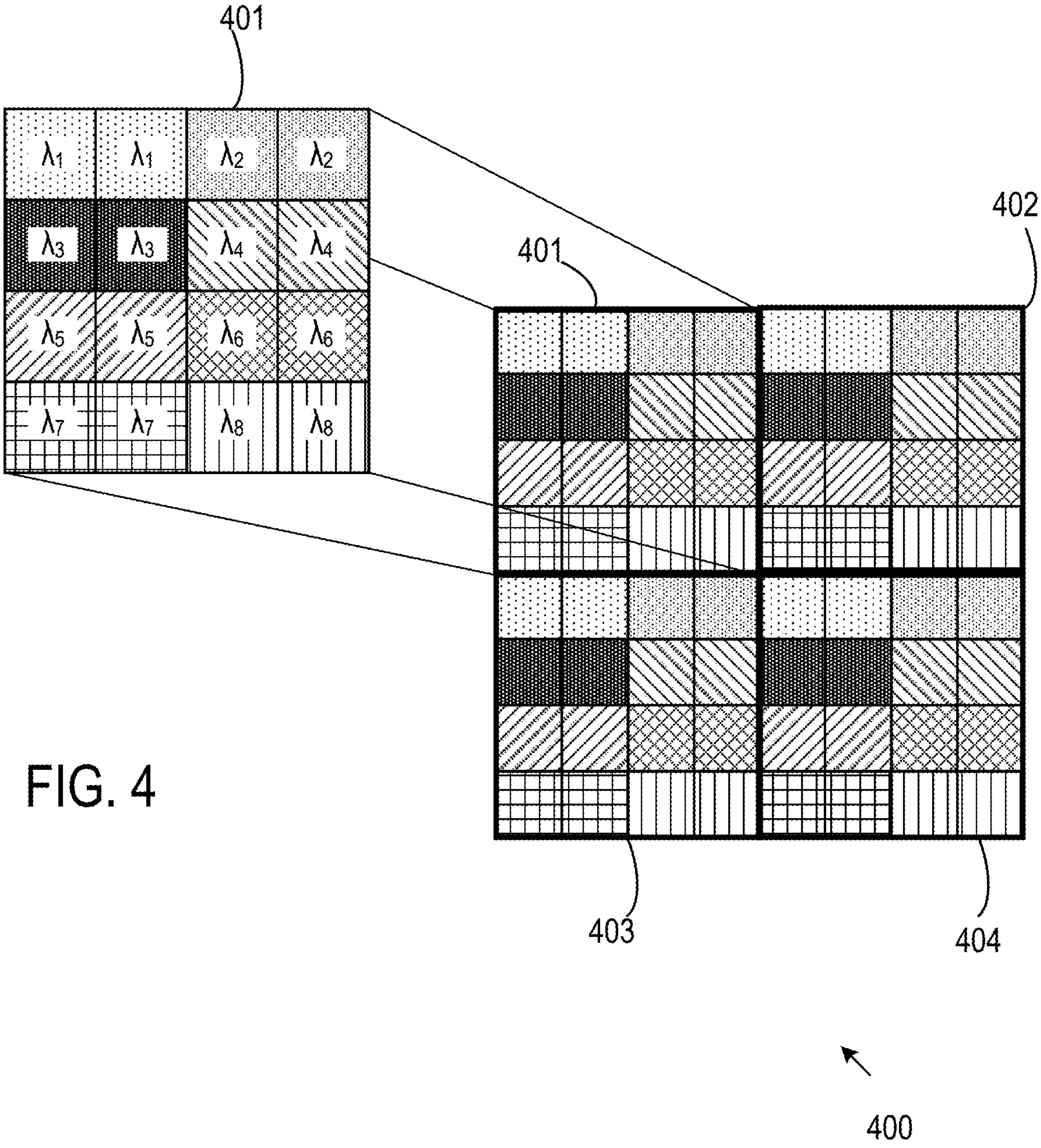

In some examples hyperspectral cameras that provide a number of spectral channels can be used to acquire EEM data. Referring to FIG. 4, a portion 400 of a sensor array of one example of such a camera includes representative pixels 401-404, each of which includes two sensor elements for each of eight different wavelengths. In typical arrangements, pixels and sensor elements are separated by inactive regions but these are not shown in FIG. 4. The pixel 401 includes two sensor elements for each wavelength (or range) $\lambda_1$-$\lambda_8$. Pixels 402-404 are of similar construction and spectral sensitivity is shown with shading to correspond with the pixel 401. Only four pixels are shown, but one commercial 8-channel hyperspectral digital camera can record emission spectra for 256×256 pixels for eight emission wavelengths. Higher emission spectral resolutions can be achieved by spectrally scanning emission wavelengths by scanning over an emission wavelength range (spectral scanning) or spatially scanning the sample and imaging by pushbroom imaging.

Example 6. Representative EEM System with Coded Emitters

Figure 5:
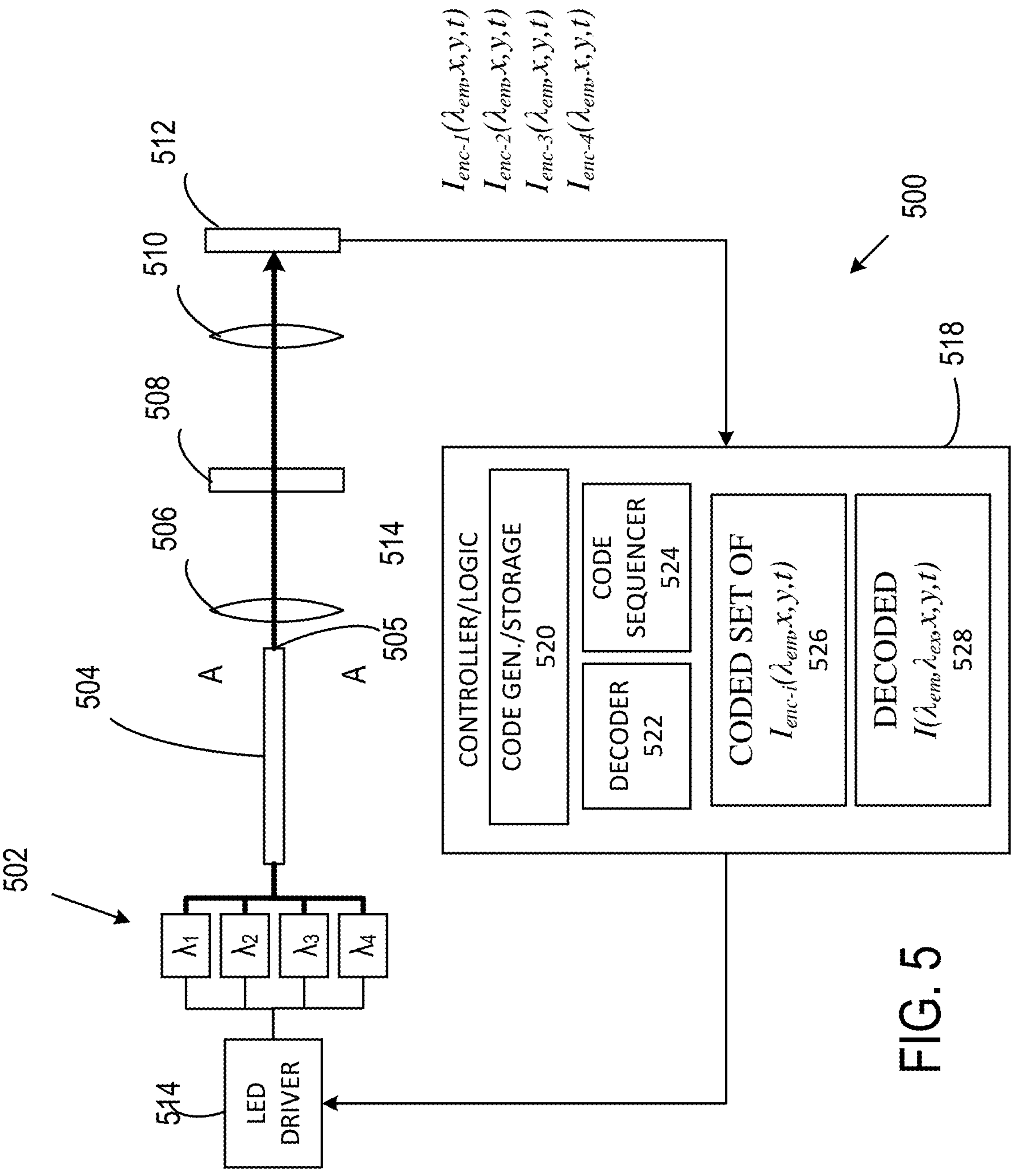
FIG. 5 illustrates a system for obtaining excitation-emission spectra using LEDs.

Referring to FIG. 5, a representative spectral emission imaging system 500 includes a set of emitters 502 such as LEDs, laser diodes, or other light sources that selectively produce coded beams at selected sets of wavelengths $\lambda_1$-$\lambda_4$ that are coupled into a light guide 504 for delivery to a specimen 508 by an optical system 506, illustrated for convenience as a single lens element. An optical system 510 illustrated also as a single lens element directs emission responsive to the coded beams to a hyperspectral camera 512. A control system 518 is coupled to an LED driver 514 that selectively activates sets of LEDs from the set 502 in response to codes generated by processor-executable instructions or codes stored at 520 and selected at 524. The spectral intensities responsive to each code can be stored at 526 and procedures for decoding stored at 522. The resulting excitation-emission matrix can be obtained by decoding and stored at 528. In some cases it is preferable to analyze the encoded spectral emission, for example, with the intent to identify chemical constituents of the sample.

Example 7. Representative EEM System with Pushbroom Imaging

Figure 6:
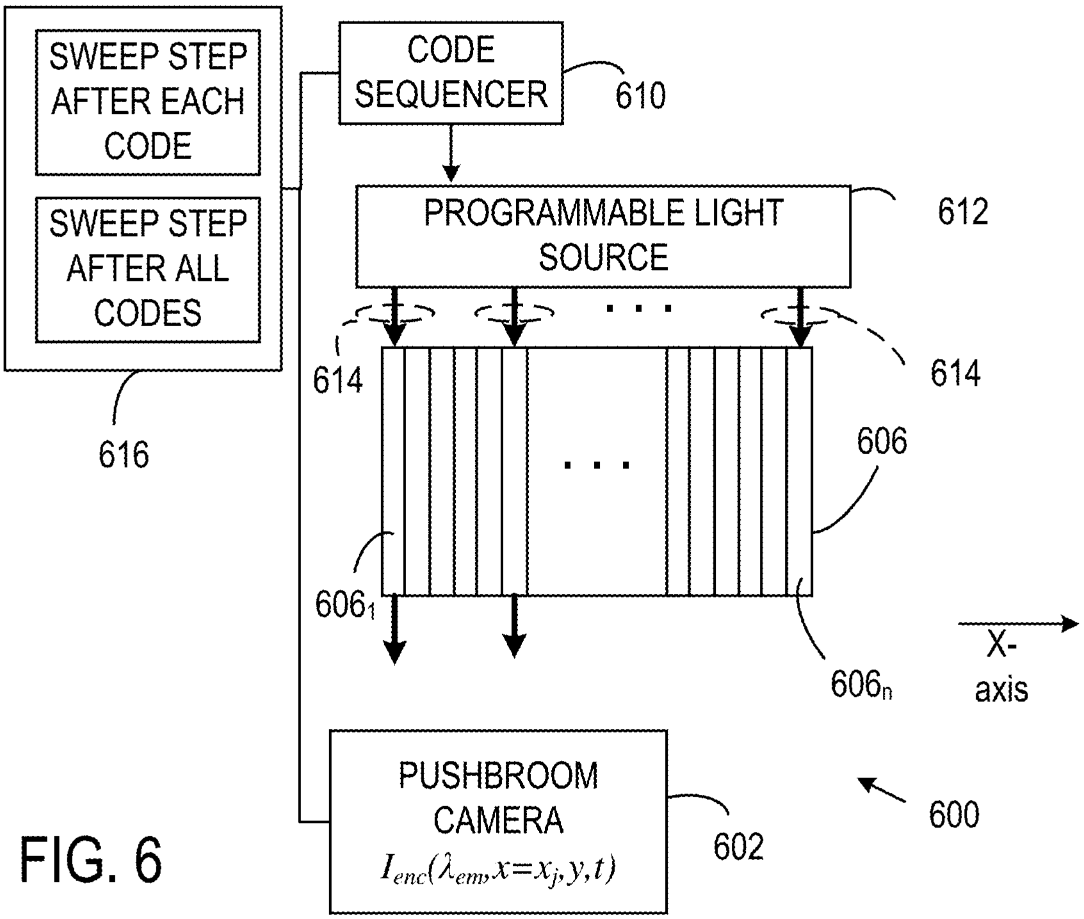
FIG. 6 illustrates a representative system for obtaining excitation-emission matrix spectra using pushbroom imaging.

Referring to FIG. 6, a system 600 includes a pushbroom camera 602 operable to sweep to sequentially form images of a strips $606_1, \ldots, 606_n$ of a specimen 606. A code sequencer 610 is coupled to a programmable light source 612 to produce coded beams 614. Logic 616 is operable to control image acquisition and coding. As shown, a scan is conducted along an X-axis to obtain $I_{enc}(\lambda_{em}, x=x_j, y, t)$. Each single strip (i.e., strips at a selected $x_j$) can be imaged with all code words prior to imaging of a subsequent strip, or a sweep can be made in which all strips are imaged with each code word prior to imaging with a subsequent code word (i.e., a strip at each $x_j$ is imaged with a selected code word prior to imaging with a subsequent code word.

Example 8. Computing Environment

Figure 7:
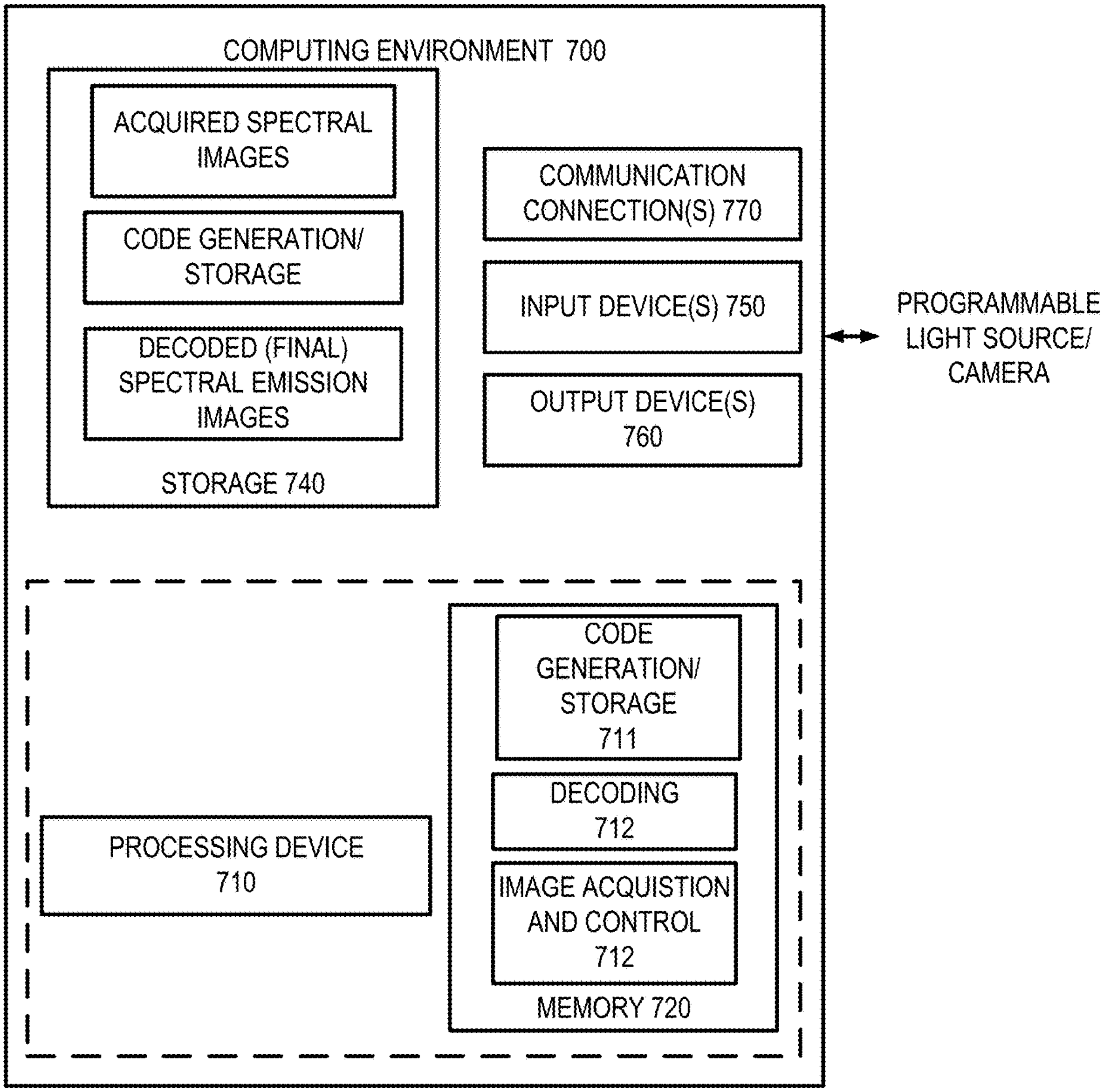
FIG. 7 illustrates a representative computing environment for system control, coding, image acquisition and storage, and decoding.

FIG. 7 illustrates a generalized example of a suitable computing environment 700 in which aspects of the described embodiments can be implemented. The computing environment 700 is not intended to suggest any limitation as to the scope of use or functionality of the disclosed technology, as the techniques and tools described herein can be implemented in diverse general-purpose or special-purpose environments that have computing hardware usings application specific integrated circuits (ASICs), floating point gate arrays (FPGAs), complex programmable logic devices (CPLDs), or other logic hardware.

With reference to FIG. 7, the computing environment 700 includes at least one processing device 710 and memory 720. The processing device 710 (e.g., a CPU or microprocessor) executes computer-executable instructions. The memory 720 may be volatile memory (e.g., registers, cache, RAM, DRAM, SRAM), non-volatile memory (e.g., ROM, EEPROM, flash memory), or some combination of the two. The memory 720 stores processor executable instructions and/or storage for generating codes 711, decoding 712, and image acquisition and instrument control. The computing environment can have additional features. For example, the computing environment 700 includes storage 740, one or more input devices 750, one or more output devices 760, and one or more communication connections 770. An interconnection mechanism (not shown), such as a bus, controller, or network, interconnects the components of the computing environment 700. Typically, operating system software (not shown) provides an operating environment for other software executing in the computing environment 700, and coordinates activities of the components of the computing environment 700.

The storage 740 can be removable or non-removable, and includes one or more magnetic disks (e.g., hard drives), solid state drives (e.g., flash drives), CD-ROMs, DVDs, or any other tangible non-volatile storage medium which can be used to store information, and which can be accessed within the computing environment 700. The storage 740 can also store instructions for spectral emission image acquisition such as providing coded excitation, storage of acquired encoded spectral images, timing of coding and image acquisition, decoding, and other operations.

The input device(s) 750 can be a touch input device such as a keyboard, touchscreen, mouse, pen, trackball, a voice input device, a scanning device, or another device that provides input to the computing environment 700. The output device(s) 760 can be a display device (e.g., a computer monitor, laptop display, smartphone display, tablet display, netbook display, or touchscreen), printer, speaker, or another device that provides output from the computing environment 700.

The communication connection(s) 770 enable communication over a communication medium to programmable light sources, control systems, and image acquisition systems such as cameras. The communication medium conveys information such as computer-executable instructions or other data in a modulated data signal. A modulated data signal is a signal that has one or more of its characteristics set or changed in such a manner as to encode information in the signal. By way of example, and not limitation, communication media include wired or wireless techniques implemented with an electrical, optical, RF, infrared, acoustic, or other carrier.

Additional Disclosure Clauses

Clause 1 is a multi-spectral imaging system, including: at least one excitation light source that produces an excitation beam having an excitation light spectrum; a multiplexer that divides the excitation beam into a plurality of excitation wavelength ranges and sequentially selects three or more excitation wavelength ranges from the plurality of excitation wavelength ranges based on code words defined by a selected code to produce a sequence of encoded excitation beams, wherein the multiplexer sequentially directs each of the encoded excitation beams to a sample location; an imaging system comprising of an image sensor having an array of pixels and situated to produce spectral images of a sample associated with a three or more wavelength ranges corresponding to each of the encoded excitation beams; and a logic processor operable to receive the images of the sample corresponding to each of the encoded excitation beams and decode the images of the sample for each pixel of the array of pixels based on the selected code to produce images corresponding to emitted intensity as a function of each excitation wavelength range and emission wavelength range for each pixel.

Clause 2 includes the subject matter of any Clause 1, and further includes a hyperspectral camera that is operable to produce excitation-encoded spectral emission images associated with each of the encoded excitation beams, wherein the logic processor is operable to decode the excitation-encoded spectral emission images associated with each of the encoded excitation beams to produce respective excitation emission images associated with each of a for or more emission wavelengths and a three or more excitation wavelengths.

Clause 3 includes the subject matter of any of Clauses 1-2, and further specifies that the multiplexer includes a diffraction grating or other dispersion element such as a prism situated to divide the excitation beam into the plurality of excitation wavelength ranges and a spatial light modulator situated to sequentially select three or more excitation wavelength ranges from the plurality of excitation wavelength ranges.

Clause 4 includes the subject matter of any of Clauses 1-3, and further specifies that the spatial light modulator is a digital micromirror device.

Clause 5 includes the subject matter of any of Clauses 1-4, and further specifies that the spatial light modulator is a liquid crystal spatial light modulator.

Clause 6 includes the subject matter of any of Clauses 1-5, and further specifies that the code words are based on a Hadamard code.

Clause 7 includes the subject matter of any of Clauses 1-6, and further specifies that the selected code is based on an orthogonal code.

Clause 8 includes the subject matter of any of Clauses 1-7, and further specifies that the image sensor is snapshot spectral imager.

Clause 9 includes the subject matter of any of Clauses 1-8, and further specifies that the spectral images are based on at least one of luminescence, absorption, reflection, and elastic and inelastic scattering.

Clause 10 is a multi-spectral imaging method, including:
- directing a sequence of spectrally encoded excitation beams to a sample, wherein the spectrally encoded excitation beams are associated with a plurality of excitation wavelength ranges; in response to each of the spectrally encoded excitation beams, obtaining excitation-encoded spectral emission images for a plurality of emission wavelength ranges; and decoding the excitation-encoded spectral emission images to produce excitation-emission images associated with the plurality of excitation wavelength ranges and the plurality of emission wavelength ranges.

Clause 11 includes the subject matter of Clause 10, where the spectrally encoded excitation beams are produced with a spatial light modulator.

Clause 12 includes the subject matter of any of Clauses 10-11, where the excitation-encoded spectral emission images are obtained with a hyperspectral camera.

Clause 13 includes the subject matter of any of Clauses 10-12, where the spectrally encoded excitation beams are produced with a digital mirror device.

Clause 14. The multi-spectral imaging method of claim 10-13, and further includes producing excitation-emission images associated with the plurality of excitation wavelength ranges and the plurality of emission wavelength ranges at a series of times.

Clause 15 includes the subject matter of any of Clauses 10-14, and further includes storing the excitation-emission images associated with the plurality of emission wavelength ranges at a series of times as at least one image sequence.

Clause 16 includes the subject matter of any of Clauses 10-15, and further specifies that the spectrally encoded excitation beams are based on a Hadamard code or an orthogonal code.

Clause 17 includes the subject matter of any of Clauses 10-16, and further specifies that the spectral images are associated with at least one of luminescence, absorption, reflection, and elastic or inelastic (Raman) scattering and transmission.

Clause 18 is a multi-spectral imaging method, including:
- directing a sequence of spectrally encoded excitation beams to a sample, wherein the spectrally encoded excitation beams are associated with a plurality of excitation wavelength ranges; in response to each of the spectrally encoded excitation beams, obtaining excitation-encoded spectral emission images for a plurality of emission wavelength ranges; and decoding the excitation-encoded spectral emission images to produce excitation-emission images associated with the plurality of excitation wavelength ranges and the plurality of emission wavelength ranges; and wherein the excitation-encoded spectral emission images contain information on a chemical composition of the sample and are based on by at least one of luminescence, absorption, reflection, transmission, and elastic or inelastic (Raman) scattering and transmission.

Clause 19 includes the subject matter of Clause 18, and further specifies that the spectrally encoded excitation beams are provided by selective excitation of a plurality of light emitting diodes or laser diodes, or a combination of light emitting diodes and laser diodes based on a code.

Clause 20 includes the subject matter of any of Clauses 18-19, and further specifies that the spectrally encoded excitation beams are provided based on a linear array of light emitting diodes that produces an output beam that is spectrally dispersed and modulated with a spatial light modulator based on a code.

General Terminology

As used herein, image refers to a visual image presented for viewing on, for example, a computer display and also refers to a stored representation that can be used to produce a visual image such as a TIFF, JPEG, BMP or other format that is stored in a computer-readable memory. Typically, such stored images contain or can be processed to provide an image intensity I at each of a plurality of detector pixels which corresponds to an image intensity I(x, y) and typically as $I(\lambda_{em}, \lambda_{ex}, x, y, t)$, i.e., emitted image intensities at emission wavelength $\lambda_{em}$, as functions of excitation wavelength $\lambda_{ex}$, coordinates (x, y) and time t. Image intensities can be stored in a suitable format such as an uncompressed video format or as a series of images. As used herein, images are referred to as encoded or excitation encoded if responsive to a spectrally encoded excitation beam and are expressed as $I_{enc}(x, y, t)$. Such excitation encoded images (based on a suitable selection of code words) can be decoded to produce images referred to as excitation images associated with emission responsive to particular excitation wavelength ranges, expressed as $I(\lambda_{ex}, x, y, t)$. Spectral emission images are images associated with emission wavelength ranges and can be expressed as $I(\lambda_{em}, x, y, t)$. Spectral emission images can be obtained in response to an encoded excitation beam and their intensities can be expressed as $I_{enc}(\lambda_{em}, x, y, t)$, and can be referred to as excitation-encoded spectral emission images. Sets of excitation-encoded spectral emission images can be decoded to produce excitation-emission matrix images which provide image intensity, in particular emission wavelength ranges in response to excitation at particular wavelength ranges and can be expressed as $I(\lambda_{em}, \lambda_{ex}, x, y, t)$. Wavelength ranges (emission or excitation) can have common or different spectral widths and need not be spectrally adjacent. Suitable ranges can depend on a specimen of interest. Images are referred to above as functions of time, but in some cases images at only a selected time point are obtained.

Coded excitations beams can be produced using spatial light modulators in combination with dispersive optical elements such as diffraction gratings and prisms or using light sources include multiple LEDs or lasers that can be selectively activated based on a selected code word.

As used herein, multiplexer and multiplexing refer to systems or devices that are operable to produce coded excitation beams. Multiplexers can be based on spectral dispersion of a broadband optical beam and selection of spectral components of the broadband optical beam or by selective modulation of narrowband spectral emitters, or combinations of these approaches. For example, a spectral dispersion element (such as a prism or grating) in combination with a spatial light modulator can produce a coded excitation beam from a white light source. In another example, a set of LEDS or laser diodes having different emission wavelengths can be selectively modulated to produce a coded beam. These approaches can be combined so that some spectral portions of an excitation beam are produced with direct modulation of narrowband sources while others are produced by modulation of a broadband optical beam.

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

For convenience, the examples are described with reference to codes of length 4, but in typical examples, longer codes are preferred as signal-to-noise ratio improves based on the square root of the code length for long codes. Code generation and decoding are described in detail in in Loock et al., U.S. Pat. No. 10,481,092, incorporated by reference above. Other binary or non-binary codes such any set of linearly independent codes or Golay codes, but Hadamard-based codes reduced to 0,1 codes are generally preferred as easily generated and producing improved signal-to-noise ratios.

As used herein, multi-spectral imaging refers to imaging based at least three spectral components while hyperspectral imaging refers to imaging based at least four spectral components, although typically many more. Practical advantages of the discloses approaches tend to be more apparent with application to hyperspectral imaging. In the drawings, optical beams and optical paths are indicated with lines that are heavier than those used for electrical connections, whether wired or wireless.

As used herein, "programmable light source" or "PLS" refers to a system or apparatus that is operable to produce coded excitation beams. A PLS can be based on a broadband light source in combination with a spectral dispersion element and a suitable modulator such as a spatial light modulator. In other examples, a PLS is based on selectively modulation of multiple narrowband emitters such as LEDs or lasers. In some disclosed examples, a programmable light source has 31 to 127 distinct excitation wavelengths and full image acquisition is based on code words of a code set that encompasses all of these wavelengths, with codes of corresponding lengths. Acquisition time is typically based on camera response times. It will be appreciated that a number of excitation wavelengths generally determines preferred code length, not the number of emission wavelengths measured by the camera.

In some examples, values, procedures, or apparatus are referred to as "lowest," "best", "minimum," or the like. It will be appreciated that such descriptions are intended to indicate that a selection among many used functional alternatives can be made, and such selections need not be better, smaller, or otherwise preferable to other selections.

We claim:

1. A multi-spectral imaging system, comprising:

a programmable light source that includes at least one excitation light source that produces an excitation beam having an excitation light spectrum and operable to select three or more excitation wavelength ranges from a plurality of excitation wavelength ranges based on code words defined by a selected code to produce a sequence of encoded excitation beams, and sequentially direct each of the encoded excitation beams to a sample location; and an imaging system comprising of an image sensor having an array of pixels and situated to produce a sequence of spectral images of a sample, each sample image of the sequence of spectral images associated with a plurality of wavelength ranges corresponding to a respective encoded excitation beam.

2. The multi-spectral imaging system of claim 1, further comprising a logic processor operable to receive the spectral images of the sample corresponding to each of the encoded excitation beams and characterize the sample based on the encoded excitation beams.

3. The multi-spectral imaging system of claim 1, further comprising a logic processor operable to receive the spectral images of the sample corresponding to each of the encoded excitation beams and decode the spectral images of the sample for each pixel of the array of pixels based on the selected code to produce images corresponding to emitted intensity as a function of each excitation wavelength range and emission wavelength range for each pixel.

4. The multi-spectral imaging system of claim 3, further comprising a hyperspectral camera that is operable to produce excitation-encoded spectral emission images associated with each of the encoded excitation beams, wherein the logic processor is operable to decode the excitation-encoded spectral emission images associated with each of the encoded excitation beams to produce respective excitation emission images associated with each of a plurality of emission wavelengths and a plurality of excitation wavelengths.

5. The multi-spectral imaging system of claim 3, wherein the programmable light source includes a dispersion element situated to divide the excitation beam into the plurality of excitation wavelength ranges and a spatial light modulator situated to sequentially select three or more excitation wavelength ranges from the plurality of excitation wavelength ranges.

6. The multi-spectral imaging system of claim 5, wherein the spatial light modulator is a digital micromirror device.

7. The multi-spectral imaging system of claim 5, wherein the spatial light modulator is a liquid crystal spatial light modulator.

8. The multi-spectral imaging system of claim 3, wherein the code words are based on a Hadamard code.

9. The multi-spectral imaging system of claim 3, wherein the selected code is based on an orthogonal code.

10. The multi-spectral imaging system of claim 3, wherein the image sensor is snapshot spectral imager.

11. The multi-spectral imaging system of claim 1, wherein the spectral images are based on at least one of luminescence, absorption, reflection, elastic scattering, and inelastic scattering.

12. A multi-spectral method, comprising:

directing a sequence of spectrally encoded excitation beams to a sample, wherein the spectrally encoded excitation beams are associated with a plurality of excitation wavelength ranges; and in response to each of the spectrally encoded excitation beams, obtaining excitation-encoded spectral emission images of a sample for a plurality of emission wavelength ranges.

13. The multi-spectral method of claim 12, further comprising characterizing the sample based on the excitation-encoded spectral emission images.

14. The multi-spectral method of claim 12, further comprising decoding the excitation-encoded spectral emission images to produce excitation-emission images associated with the plurality of excitation wavelength ranges and the plurality of emission wavelength ranges.

15. The multi-spectral method of claim 14, further comprising characterizing the sample based on the excitation-emission images.

16. The multi-spectral method of claim 12, where the spectrally encoded excitation beams are produced with a spatial light modulator.

17. The multi-spectral method of claim 12, where the excitation-encoded spectral emission images are obtained with a hyperspectral camera.

18. The multi-spectral method of claim 12, where the spectrally encoded excitation beams are produced with a digital mirror device.

19. The multi-spectral method of claim 12, further comprising producing excitation-emission images associated with the plurality of excitation wavelength ranges and the plurality of emission wavelength ranges at a series of times.

20. The multi-spectral method of claim 19, further comprising storing the excitation-emission images associated with the plurality of emission wavelength ranges at a series of times as at least one image sequence.

21. The multi-spectral method of claim 12, wherein the spectrally encoded excitation beams are based on a Hadamard code or an orthogonal code.

22. The multi-spectral method of claim 12, wherein the excitation-encoded spectral emission images are associated with at least one of luminescence, absorption, reflection, transmission, elastic scattering, and inelastic scattering.

23. A multi-spectral imaging method, comprising:

directing a sequence of spectrally encoded excitation beams to a sample, wherein the spectrally encoded excitation beams are associated with a plurality of excitation wavelength ranges;

in response to each of the spectrally encoded excitation beams, obtaining excitation-encoded spectral emission sample images for a plurality of emission wavelength ranges; and decoding the excitation-encoded spectral emission sample images to produce excitation-emission sample images associated with the plurality of excitation wavelength ranges and the plurality of emission wavelength ranges; and wherein the excitation-encoded spectral emission sample images contain information on a chemical composition of the sample and are based on by at least one of luminescence, absorption, elastic scattering, inelastic scattering, and transmission.

24. The multi-spectral imaging method of claim 23, wherein the spectrally encoded excitation beams are provided by selective excitation of a plurality of light emitting diodes, lasers diodes, or a combination of light emitting diodes and laser diodes based on a code.

25. The multi-spectral imaging method of claim 23, wherein the spectrally encoded excitation beams are provided based on a linear array of light emitting diodes or lasers that produces an output beam that is spectrally dispersed and modulated with a spatial light modulator based on a code.

* * * * *